United States Patent
Deshpande et al.

(10) Patent No.: US 10,532,035 B2
(45) Date of Patent: Jan. 14, 2020

(54) METHODS FOR IMPROVEMENT OF VISUAL FUNCTION AND COMPOSITIONS USED THEREIN

(71) Applicant: OmniActive Health Technologies Limited, Mumbai (IN)

(72) Inventors: Jayant Deshpande, Charlottetown (CA); Vijaya Juturu, Morristown, NJ (US); Khadija Ghanam, Charlottetown (CA); Lynda Doyle, Morristown, NJ (US)

(73) Assignee: OmniActive Health Technologies Limited, Mumbai (IN)

( * ) Notice: Subject to any disclaimer, the term of this patent is extended or adjusted under 35 U.S.C. 154(b) by 0 days.

(21) Appl. No.: 15/081,272

(22) Filed: Mar. 25, 2016

(65) Prior Publication Data

US 2016/0279076 A1    Sep. 29, 2016

Related U.S. Application Data

(60) Provisional application No. 62/138,826, filed on Mar. 26, 2015.

(51) Int. Cl.
*A61K 31/047* (2006.01)

(52) U.S. Cl.
CPC .................................. *A61K 31/047* (2013.01)

(58) Field of Classification Search
None
See application file for complete search history.

(56) References Cited

U.S. PATENT DOCUMENTS

| | | |
|---|---|---|
| 8,603,522 B2 | 12/2013 | Bartels et al. |
| 2011/0052511 A1 | 3/2011 | Goralczyk et al. |
| 2011/0065805 A1 | 3/2011 | Kumar et al. |
| 2013/0011486 A1 | 1/2013 | Nolan et al. |
| 2013/0231297 A1 | 9/2013 | Krawitz |
| 2013/0296442 A1 | 11/2013 | Barker et al. |
| 2014/0221487 A1 | 8/2014 | Renzi et al. |

FOREIGN PATENT DOCUMENTS

| | | |
|---|---|---|
| CN | 101757299 | 6/2010 |
| WO | 2013009378 | 1/2013 |
| WO | 2013043366 | 3/2013 |
| WO | 2015175478 | 11/2015 |

OTHER PUBLICATIONS

Chang et al., PNAS, Jan. 27, 2015, vol. 112(4), pp. 1232-1237. (Year: 2015).*
Bernstein et al., Vision Research, 2010, vol. 50, pp. 716-728.*
"FloraGLO® Lutein: Eye Health Supplement Ingredient", downloaded on Mar. 1, 2019 from "https://www.kemin.com/na/en-us/products/floraglo-lutein", 5 pages.*
"Kemin & DSM Expand Partnership with OPTISHARP Natural", downloaded on Mar. 1, 2019 from "https://www.nutraceuticalsworld.com/issues/2014-11/view_industry-news/kemin-dsnn-expand-partnership-with-optisharp-natural/1314", 1 page.*
International Search Report and Written Opinion, issued in the corresponding PCT application No. PCT/IB2016/051730, dated Aug. 8, 2016, 8 pages.

* cited by examiner

*Primary Examiner* — Savitha M Rao
*Assistant Examiner* — Gregg Polansky
(74) *Attorney, Agent, or Firm* — Hamre, Schumann, Mueller & Larson, P.C.

(57) ABSTRACT

Methods herein are described for improvement in visual function by administering macular carotenoid compositions containing an effective daily dose, to a subject in need thereof. More particularly, methods herein are described and include use of the compositions herein by identifying a subject in need thereof, administering a daily dose of lutein and/or zeaxanthin isomers, comprised of meso-zeaxanthin and R,R zeaxanthin, alone or in combination thereof, the composition also including at least one food grade excipient, and evaluating visual performance. The subject is exposed to light of variable wavelengths and intensity and is suffering from visual fatigue. The composition improves contrast sensitivity, glare performance, photo stress recovery, and/or macular pigment optical density, and thus alleviates visual fatigue. The composition is safe for human and other animals for consumption and can be used for improvement in visual health in the subject, when administered in an effective amount.

9 Claims, 11 Drawing Sheets

Carotenoid composition increased Contrast sensitivity over placebo

Disability Glare_ composition Improved Glare performance

Composition improved better photo stress recovery

Change from baseline: composition improved MPOD over Placebo

METHODS FOR IMPROVEMENT OF VISUAL FUNCTION AND COMPOSITIONS USED THEREIN

FIELD

Methods herein are described for prevention and treatment of visual fatigue by administering macular carotenoid compositions containing an effective daily dose, to a subject in need thereof. The compositions herein are comprised of macular carotenoids selected from the group of lutein, meso-zeaxanthin, zeaxanthin, isomers, metabolites, esters, salts, derivatives either alone, or in combinations thereof, along with one or more food grade excipients, such as fat, fatty acid, oil, antioxidant, vitamin, and the like and the combinations thereof. More particularly, methods herein are described and include use of the compositions herein for identifying a subject in need thereof, administering a daily dose of at least 1 mg of lutein, and/or at least 0.2 mg zeaxanthin isomer(s), which are comprised of meso-zeaxanthin and R,R zeaxanthin, either alone or in combination thereof, along with at least one food grade excipient, and evaluating visual performance of the subject. The subject in need thereof is exposed to light of variable wavelengths and intensity, such as blue light from electronic devices, ultraviolet rays, and/or any other light emitting source for an extended time period and/or under routine living and working conditions, and is suffering from visual fatigue, visual stress, visual discomfort, and/or affected sleep quality. The methods described herein help to prevent and treat visual fatigue by improving speed of processing, adaptation with low light conditions and sleep pattern. The compositions herein also improve contrast sensitivity, glare performance, photo stress recovery and/or macular pigment optical density, and thus can alleviate visual fatigue. The compositions herein are safe for humans and other animals for consumption and can be used for improvement in visual performance in the subject in need thereof, when administered ineffective amounts, which can include an effective daily dose.

BACKGROUND

The eyes are an important, but often overlooked part of the body. Despite the preventable nature of some vision impairments, many people do not receive recommended regular screenings and exams and therefore may be subject to and/or contract common visional problems such as diabetic retinopathy, glaucoma, cataract, and age related macular degeneration. These common vision problems often do not provide any early warning signs. If some basic eye care is taken and routine examination is carried out, eye problems can be detected at early stage and corrective measures can be taken to minimize vision loss and help a person see his or her best. Such healthy vision can help keep people safe when behind the wheel, participating in sports, and/or working with computers in the office or power tools in their yard or around their home.

Nowadays, people of all age group extensively use electronic devices such as laptops, computers, tablets, cell phones for extended time periods ranging from 4 to 10 hours, which emit blue light of varying intensity. Even children use electronic devices with screens or displays, such as televisions, tablets, video games, other entertainment equipment for prolonged time during day as well as during night hours, even before going to bed. People are also exposed to sun rays and other light sources in routine life such as traffic signals, road lights, cinema theatre or cricket ground lights which cause visual fatigue, stress and discomfort, thus affecting overall visual performance over time period. Exposure to blue light from electronic devices at night time also affects quality of sleep and puts extra stress on visual function, while carrying out visual activities at work place.

Many people who use computers for extended time periods such as 8 to 10 hours a day complain of eye strain. They also experience symptoms such as eye discomfort, headaches, soreness, tiredness, burning or itchiness in the eyes, and/or watery or dry eyes, thus further aggravating the problems in the form of difficulty in focusing, blurred or double vision, and/or increased photosensitivity to eyes. Medical intervention is then needed to treat these conditions and even though many treatment options like lubricating eye drops, antibiotic drops, ointments, and related eye care drugs are available, ophthalmologists still prefer the option of advising their patients to avoid prolonged use of electronic devices and take some basic care such as washing eyes in between the use or having some eye exercises to avoid visual strain. Proper diet comprised of fruits, green vegetables, egg yolks, and raw salads is also advised in order to provide precursors of vitamin A, which is supposed to be beneficial along with omega-3 fatty acids and other antioxidants, for protecting vision health (Ref- Dr. Yves Sauvé—Article-Nutrition and Vision Health).

Many references report use of natural supplements for treatment of visual health.

US20110052511A1 relates to compositions, preferably an orally applicable composition, having an effective amount of at least one compound selected from the group consisting of β-carotene, lutein, lycopene and β-cryptoxanthin and mixtures thereof and combinations thereof with CoQ-10 as active ingredient(s), characterized in that the amount is effective for maintaining the energy metabolism, the energy flow and/or the energy production in skin or of skin of animals including humans, for maintaining the respiratory function of the skin of animals including humans, for energizing the skin, maintaining and supporting the radiance and natural glow of the skin of the animals including humans and for promoting a healthy appearance of the skin of the animals including humans and for preventing UV-A radiation-induced mitochondrial DNA (mtDNA) mutagenesis in skin of the animals including humans.

US20130296442A1 relates to improvement of visual performance, particularly of visual performance in darkness, by administration of a colorant that is capable of being incorporated into eye tissue and/or causing yellowing of eye tissue, especially carotenoids, such as lutein and zeaxanthin. The reference aims to improve visual performance in darkness and not in exposure of light.

U.S. Pat. No. 8,603,522B2 relates to a method for stabilizing visual acuity loss in people having early age related macular degeneration by administering a daily dosage of not less than approximately 420 mg and not more than approximately 600 mg of vitamin C, not less than approximately 400 IU and not more than approximately 540 IU of vitamin E, approximately 0.04 mg to 40 mg of lutein-zeaxanthine combination, not less than approximately 60 mg and not more than approximately 100 mg of zinc and at least 1.6 mg and not more than approximately 2.4 mg of copper.

WO2013043366A1 relates to use of composition of lutein, zeaxanthin, beta-carotene, astaxanthin, vitamin C, and vitamin E for improving visual function and eye health in an animal. Though the patent document relates to improvement of visual performance, it does not demonstrate the eye-brain coordination to reduce the eye fatigue and eye strain under specific conditions or with a high energy source.

CN101757299A relates to a composition for relieving visual fatigue, wherein the composition includes components in parts by weight: 22-28 parts of eyebright, 20-26 parts of xanthan, 14-18 parts of huckleberry, 15-20 parts of ginkgo leaves, 16-22 parts of grape pips, 1-5 parts of zinc lactate and 1-5 parts of vitamin A. Particularly, a composition has effects of preventing, improving and treating blurred vision, dry eye syndrome, swollen pain of eyes, photophobia and the like.

WO 2013009378 A1 (University of Georgia) relates to a method of enhancing a subject's macular pigment optical density by administering to the subject a pharmaceutically effective amount of one or more xanthophyll carotenoids. Preferably, the xanthophyll carotenoids are selected from the group consisting of lutein (L), zeaxanthin (Z), and mesozeaxanthin (MZ), and enantiomers, metabolites, esters, pharmaceutically acceptable salts and derivatives thereof. In certain embodiments, the xanthophyll carotenoids such as lutein (L), zeaxanthin (Z), and mesozeaxanthin (MZ) are each in substantially pure enantiomeric form.

PCT application WO2015175478 relates to a dietary supplement composition which is formulated in a therapeutically effective amount to treat the eye of an individual having an eye impairment, including dry eyes. It includes a mixture of a phospholipid and a seed oil extract, astaxanthin, and at least one carotenoid selected from the group consisting of lutein, trans-zeaxanthin, and meso-zeaxanthin. It is formulated into a single dosage capsule.

Patent publication US20130231297 describes an orally administered composition for improving visual performance, said composition comprising a combination of astaxanthin, saffron, lutein, zeaxanthin and European black currant extract, in amounts effective to reduce eye fatigue or enhance at least one of visual acuity, contrast acuity, glare relief and recovery, and high intensity blue light filtration.

PCT patent publication WO2015175478 relates to a dietary supplement composition which is formulated in a therapeutically effective amount to treat the eye of an individual having eye impairment, including dry eyes. It includes a mixture of a phospholipid and a seed oil extract, astaxanthin, and at least one carotenoid selected from the group consisting of lutein, trans-zeaxanthin, and meso-zeaxanthin. It is formulated into a single dosage capsule.

US20130231297 describes an orally administered composition for improving visual performance, said composition comprising a combination of astaxanthin, saffron, lutein, zeaxanthin and European black currant extract, in amounts effective to enhance visual acuity.

SUMMARY

The above references do not discuss the effect of macular carotenoids alone on protecting the eye from visual fatigue and alleviating visual strain and/or fatigue caused due to exposure of eyes to light sources having different intensities and thus improving visual health. The references do not relate to the evaluation of macular carotenoids or their compositions for their effect on recovery of visual fatigue or for improvement in overall visual health of a subject in need thereof. Applicant has carried out rigorous experimentation for use of macular carotenoids compositions and evaluation the results of which demonstrate the effects on improving visual health by relieving visual fatigue, in a subject who is exposed to blue light, UV rays and light rays of varying intensities for extended time period, such study has not been reported in the references.

The composition helps to protect and improve visual health and reduces associated risk factors such as retinal tissue inflammation, disturbed eye-brain coordination, cognitive function and the like, when administered to a subject in need thereof, in effective amounts. The composition also relieves eye strain and/or fatigue by reducing oxidative stress and inflammatory markers, improving macular pigment density oxidative stress and thus improving overall eye health. Macular carotenoid compositions herein can protect and improve visual health in a subject, who is exposed to varying light intensities, such as blue light, ultraviolet (UV) light and the like, causing eye strain and/or fatigue. The composition is safe for human and other animals for consumption and can be employed for protection and improvement of visual health thereof, when administered in effective amounts.

In an embodiment, a method herein comprises identifying a subject in need of protection and/or treatment from visual fatigue, and administering a composition comprising macular carotenoids alone or in combination with other nutrients, and one or more food grade excipients. The method described herein helps to protect the eye from visual fatigue by improving parameters such as visual processing speed, contrast sensitivity, disability glare, and/or photostress recovery. The composition also improves macular pigment optical density and/or sleep quality, thus relieving visual stress and/or discomfort. The method described herein protects the eye from visual fatigue and treats the fatigue condition in a subject, who is exposed to light of varying wavelength and light intensities, such as blue light, sun rays, light rays from electronic devices, street lights, traffic lights and the like, for a prolonged time period. The composition used therein is safe for human and other animals for consumption and can be used for protection and treatment of visual fatigue thereof, when administered in an effective amount which may include an effective daily dose.

In some embodiments, methods of treatment herein are directed to administering a macular carotenoid composition in an effective amount(s) to improve visual function in a subject by preventing and/or treating visual fatigue condition caused by prolonged exposure to light sources, selected from the group of, but not limited to, blue light, sun rays/UV light, traffic lights, street lights, combinations thereof, or the like, which emit light of variable wavelength and intensities.

In some embodiments, methods of treatment herein are directed to administering a macular carotenoid composition in an effective amount to a subject in need thereof, and evaluating parameters such as visual processing speed, contrast sensitivity, disability glare, and/or photostress recovery to check the beneficial effects of macular carotenoids for protection and treatment of visual fatigue caused by exposure to light sources for prolonged time period.

In some embodiments, compositions and methods of treatment herein are directed to evaluating the effect(s) of a macular carotenoid composition on the treatment and protection from visual fatigue by administering to a subject in need thereof, an effective amount of a composition comprising macular carotenoid(s) alone or in combination with other nutrients. The macular carotenoid(s) of the composition may be lutein or zeaxanthin isomers alone, or a combination of lutein and zeaxanthin isomers, such as meso-zeaxanthin and R,R zeaxanthin.

In some embodiments, macular carotenoid compositions herein and methods of treatment using the compositions are directed to the improvement of visual health by improvement in macular pigment optical density and/or sleep quality, thus relieving visual stress and/or discomfort. The methods described herein protect the eye from visual fatigue and also treat visual fatigue in subject in need thereof such treatment, In an embodiment, a macular carotenoid composition herein is administered in a daily dose of macular carotenoids, where the dose of carotenoids is at or about 250 micrograms to at or about 100 mg of carotenoids.

In an embodiment, a macular carotenoid composition herein is administered in a daily dose of macular carotenoids, where the dose of carotenoids is at or about 250 micrograms to at or about 30 mg.

In some embodiments, macular carotenoid compositions herein and methods of treatment using the composition are directed to administering the composition, for example in a daily dose of about 100 micrograms to about 100 mg of macular carotenoids, to the subject in need thereof.

Further the composition may be administered such that, macular carotenoids contained therein are provided in a daily dose of 200 micrograms to 50 mg over a certain period of treatment in the treatment of visual fatigue and improvement of visual function.

In an embodiment, a method as described herein is directed to administering a carotenoid composition in a daily dose of macular carotenoids such that 1 mg of lutein alone, or 0.2 mg of zeaxanthin isomers alone, or the combination of 1 mg of lutein and 0.2 mg of zeaxanthin isomers comprising meso-zeaxanthin and R,R zeaxanthin are provided to a subject in need thereof, over a certain period of treatment in the treatment of visual fatigue and improvement of visual function In an embodiment, a method as described herein is directed to administering a carotenoid composition in a daily dose of macular carotenoids such that 6 mg lutein alone, or 1.5 mg zeaxanthin isomers alone, or a combination of 6 mg lutein and 1.5 mg zeaxanthin isomers is provided to subjects in need thereof, over a certain period of treatment in the treatment of visual fatigue and improvement of visual function, and who may be suffering from visual fatigue, visual stress, discomfort, affected sleep quality, and/or showing symptoms of visual fatigue. The zeaxanthin isomers comprise meso-zeaxanthin and R,R zeaxanthin.

In an embodiment, a method as described herein is directed to administering a carotenoid composition in a daily dose of macular carotenoids such that 10 mg lutein alone, or 2 mg zeaxanthin isomers alone, or a combination of 10 mg lutein and 2 mg zeaxanthin isomers is provided to subjects in need thereof, over a certain period of treatment in the treatment of visual fatigue and improvement of visual function, and who may be suffering from visual fatigue, visual stress, discomfort, affected sleep quality, and/or showing symptoms of visual fatigue. The zeaxanthin isomers comprise meso-zeaxanthin and R,R zeaxanthin.

In an embodiment, a method as described herein is directed to administering a carotenoid composition in a daily dose of macular carotenoids, such that 20 mg lutein alone, or 4 mg zeaxanthin isomers alone, or a combination of 20 mg lutein and 4 mg zeaxanthin isomers is provided to subjects in need thereof, over a certain period of treatment in the treatment of visual fatigue and improvement of visual function, and who may be suffering from visual fatigue, visual stress, discomfort, affected sleep quality, and/or showing symptoms of visual fatigue. The zeaxanthin isomers comprise meso-zeaxanthin and R,R zeaxanthin.

In an embodiment, a method as described herein is directed to administering a carotenoid composition in a daily dose of macular carotenoids such that 25 mg lutein alone, or 5 mg zeaxanthin isomers alone, or a combination of 25 mg lutein and 5 mg zeaxanthin isomers is provided to subjects in need thereof, over a certain period of treatment in the treatment of visual fatigue and improvement of visual function, and who may be suffering from visual fatigue, visual stress, discomfort, affected sleep quality, and/or showing symptoms of visual fatigue. The zeaxanthin isomers comprise meso-zeaxanthin and R,R zeaxanthin.

The methods described herein relate to administering carotenoid composition for improvement in visual function by reducing visual fatigue, relieving visual stress and/or dysfunction, improving sleep pattern and related parameters, over a period of time until the symptoms of visual fatigue are relieved, thus resulting into improvement in visual function. The compositions, as used herein may be administered for a period starting from 3 months and extending to 6 months, 12 months or 24 months. The period of administration can be extended beyond this, if required, until visual function is improved in the subjects in need thereof. In an embodiment, a treatment period of at or about 6 months to at or about 1 year is shown to provide the improvements. In embodiment, the compositions as used herein are administered in an effective amount, e.g. an effective daily dose, to the subjects in the morning time with breakfast.

The methods described herein relate to protection and treatment of visual fatigue in subjects in need thereof, such as for example mammals including a human, who are exposed to light emitting devices of various wavelengths and intensities, for a prolonged time period, by administering an effective amount of macular carotenoid composition and evaluating one or more parameters such as visual processing speed, contrast sensitivity, disability glare, and/or photostress recovery to check beneficial effects of macular carotenoids for protection and treatment of subjects for visual fatigue.

DETAILED DESCRIPTION

Figure 1:
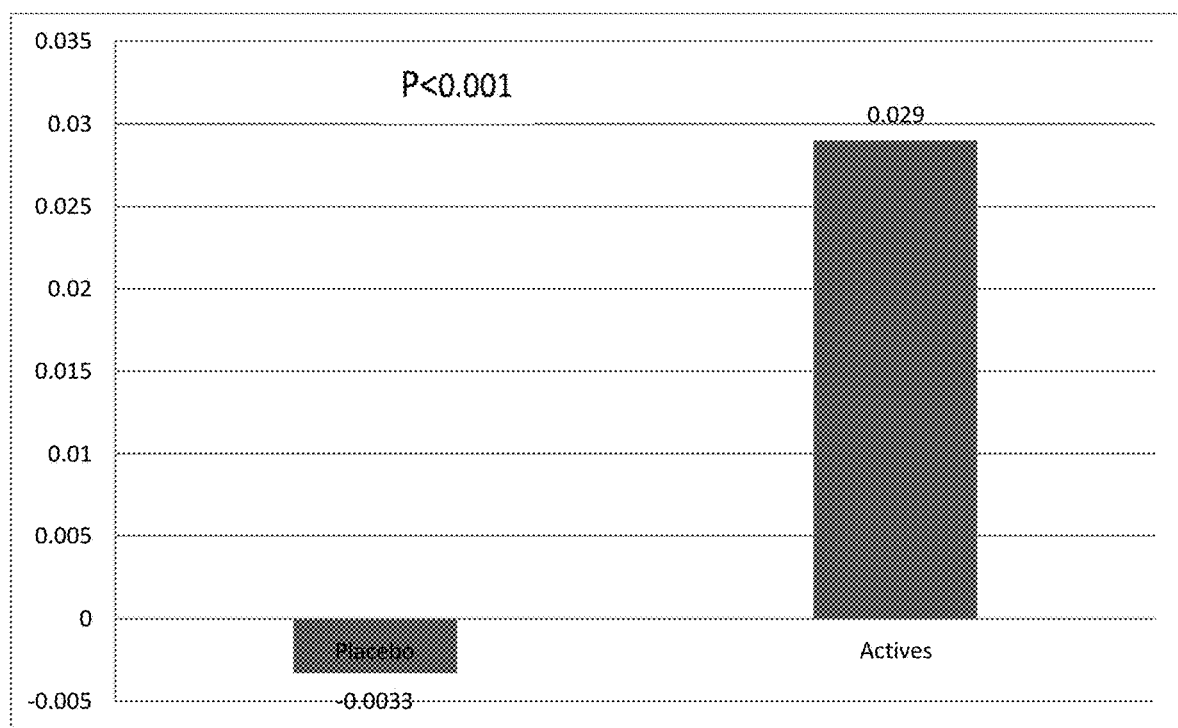
FIG. 1 shows the effect of a composition herein on macular pigment optical density (MPOD).

In environments with natural and man-made lights, the most offending portions of the electromagnetic spectrum are the Ultraviolet-A (315 nm to 400 nm), Ultraviolet-B (280 nm to 315 nm), and "blue-light" portion of the visible spectrum (380 nm to 500 nm). Additionally, as the cornea and crystalline lens absorbs almost all natural ultraviolet radiation, this radiation is thought to cause damage to the anterior eye, while short visible light ("blue-light") can cause damage to retinal structures. Exposure to damaging blue light wavelengths is thought to be responsible for everything from disrupted sleep patterns to retina damage. Blue light has very short wavelengths, and produces a higher amount of energy, which can cause more damage to the eye. We use digital devices more and more every day, and are exposed to more light emitting diode (LED) lighting and compact fluorescent lighting (CFLs)—all emit high levels of blue light. Macular pigment absorbs blue light more than green light. Blue light damages the back of the eye, causing conditions like AMD and cataracts. The light sources of varying intensities and wavelengths also put stress on the eye, thus causing visual fatigue.

The methods described herein and the compositions used are directed to improving visual health and relieving eye strain and/or fatigue by administering a macular carotenoid composition in an effective amount(s) to a subject in need thereof. The methods and compositions herein can protect, treat, and/or improve conditions associated with visual fatigue such as eye strain, eye inflammation, dry eyes, and/or visual discomfort, so as to protect eye and improve coordination with brain, when administered for example to a subject who is exposed to various light emitting devices, including but not limited to blue light, sun rays, and other lightwaves of various intensities for a prolonged time period.

The active ingredients of macular carotenoid compositions herein, for example the macular carotenoids, are obtained from natural resources and by human intervention. The compositions are safe for administration, and are useful as nutraceutical compositions and/or formulations.

Constant exposure to blue light, UV light, and other light waves of various intensities poses hazard through a modern life style and work conditions and may cause suffering of visual health to a great extent. Such people experience symptoms such as eye fatigue, eye strain, and related eye discomfort, which may have an overall impact on work performance. One of the causative factors is use of computers and laptops and exposure to blue light for extended periods of time such as for example, but not limited to 4 to 10 hours.

The terminology "subject" refers to a human individual or a mammal which may be undergoing testing, which is being treated with the macular carotenoid compositions herein.

The terminology "subject in need thereof" can include specific individuals or mammals, who may get exposed to, or may have been exposed to various light sources of variable wavelengths and intensities for a prolonged period of time such as for example but not limited to 4 to 10 hours. This causes damage to retinal cells, affects sleep quality and results into visual discomfort because of oxidative stress and inflammation in the eyes.

In some examples, a subject in need thereof may be exposed to such variable light sources of variable wavelengths, including for example a computer screen, e.g. laptop, for at or about 8 hours or more. In some examples, such exposure may be extended for days, e.g. 5 days in a week, sometimes more or less.

The term "visual fatigue" as used herein, refers to the condition of eye which is caused by prolonged exposure to light source of varying wavelength and intensities, such as electronic equipments for 4 to 10 hours and causes retinal damage, which is evident by visual discomfort, visual stress, and/or dryness in the eyes, which may result in a disturbed sleep pattern, reduced contrast sensitivity, and/or reduced photo-stress recovery, thus affecting visual health. The preliminary symptoms of visual fatigue can be alarming, and administering the compositions as described herein, in an effective amount, can provide an advantage of protecting such subjects in need thereof.

The methods herein can be used for treatment of visual fatigue in subjects in need thereof.

The term "light sources of varying wavelengths" herein means light sources generating short and long wavelengths, which are both visible and non-visible, such as for example but not limited to electromagnetic waves, ultraviolet rays, and infra-red spectrums.

Light sources of varying intensities herein mean the light sources generating both low intensity and high intensity lights. Low intensity lights are generally generated from household electronic equipments; while high intensity light sources are used in dentistry to cure adhesives and for tooth whitening (bleaching) using primarily the short visible wavelengths ("blue-light"), but also long ultraviolet wavelengths (down to 370 nm). Various type light sources can include, for example, halogen, LED, metal halide, plasma arc, and diode laser.

The term "contrast sensitivity" as used herein means the ability to differentiate between light and dark (contrast). Contrast sensitivity is a very important measure of visual function, especially in situations of low light, fog, and/or or glare, when the contrast between objects and their background often is reduced. Driving at night is an example of an activity that requires good contrast sensitivity for safety. If one is suffering from low contrast sensitivity, he/she might notice that the eyes tire more easily while reading and/or watching television.

The term "visual processing speed" as referred herein means a condition wherein the observer can no longer distinguish between changing visual stimuli, like two colors of light flickering at increasing frequencies. It is also known as critical flicker fusion (CFF), which is a valuable clinical test to estimate potential visual acuity, for example in the presence of media opacity, and/or to screen for lesions of the optic nerve.

The term "disability glare" herein means a degradation of visual performance caused by a reduction of contrast. It can affect the visual function by reducing the contrast between an object and its background.

The term "photostress recovery" as used herein is a test which is a simple clinical technique that can differentiate between retinal (macular) and post retinal (e.g. optic nerve) disease. The test involves exposing the eye to the light from the ophthalmoscope for at or about 10 seconds and measuring the time taken for acuity to return to within one line of pre-bleach acuity. Subjects with normal healthy macular function should be able to read lines within 50-60 seconds. Patients with a macular problem may have recovery times lasting 1.5 to 3 minutes or longer. In car drivers with macular degeneration, photostress effects from opposing cars may bleach retinal pigments and cause a dramatic drop in visual acuity. In patients with optic nerve disease the bleaching of the retina will have no effect on the recovery time.

In an embodiment, methods are described herein for protection and treatment of visual fatigue by administering a macular carotenoid composition to a subject in need thereof, and evaluating one or more parameters, such as for example but not limited to contrast sensitivity, glare disability, and/or photostress recovery, to assess improvement in visual function.

In one embodiment, macular carotenoid compositions herein and methods of treatment herein may include administering to a subject the macular carotenoid composition, which can be produced into a formulation, including additional nutrients such as for example but not limited to fatty acids, and/or at least one food grade excipient selected from the group of, but not limited to, an antioxidant, oil, a surfactant, a solubilizer, an emulsifier, and the like, or a combination(s) thereof.

In one embodiment, macular carotenoid compositions and methods of treatment using the composition, may comprise one or more carotenoids in various ratios, where the carotenoid(s) are lutein and zeaxanthin, either alone or in combination, and selected from the group of, but not limited to free lutein, including lutein esters and/or isomers of lutein, zeaxanthin including one or more of its isomers, such as (R,R) zeaxanthin and/or meso-zeaxanthin, and mixtures thereof.

In an embodiment, a macular carotenoid composition herein is administered in a daily dose of macular carotenoids, where the dose of carotenoids is at or about 250 micrograms to at or about 100 mg of carotenoids to a subject in need thereof.

In an embodiment, a macular carotenoid composition herein is administered in a daily dose of macular carotenoids, where the dose of carotenoids is at or about 250 micrograms to at or about 30 mg to a subject in need thereof.

In an embodiment, macular carotenoid compositions herein and methods of treatment using the compositions herein are directed to administering the composition, for example in a daily dose of macular carotenoids, where the dose of carotenoids is at or about 100 micrograms to at or about 100 mg of macular carotenoids, to the subject in need thereof.

In one embodiment, the composition may be administered such that, macular carotenoids contained therein are provided in a daily dose of at or about 200 micrograms to at or about 50 mg to a subject in need thereof.

In one embodiment, methods as described herein are directed to administering the carotenoid composition in a daily dose of macular carotenoids such that 1 mg of lutein alone, or 0.2 mg of zeaxanthin isomers alone, or the combination of 1 mg of lutein and 0.2 mg of zeaxanthin isomers comprising meso-zeaxanthin and R,R zeaxanthin to a subject in need thereof.

In an embodiment, methods described herein are directed to administering the carotenoid composition in a daily dose of macular carotenoids such that 6 mg lutein alone, or 1.5 mg zeaxanthin isomers, or a combination of 6 mg lutein and 1.5 mg zeaxanthin isomers to a subject in need thereof.

In an embodiment, methods described herein are directed to administering the carotenoid composition in a daily dose of macular carotenoids such that 10 mg lutein alone, or 2 mg zeaxanthin isomers, or a combination of 10 mg lutein and 2 mg zeaxanthin isomers to a subject in need thereof.

In an embodiment, methods described herein are directed to administering the carotenoid composition in a daily dose of macular carotenoids such that 20 mg lutein alone, or 4 mg zeaxanthin isomers, or a combination of 20 mg lutein and 4 mg zeaxanthin isomers to a subject in need thereof.

In an embodiment, methods described herein are directed to administering the carotenoid composition in a daily dose of macular carotenoids such that 25 mg lutein alone, or 5 mg zeaxanthin isomers, or a combination of 25 mg lutein and 5 mg zeaxanthin isomers to a subject in need thereof, for treatment of visual fatigue.

Compositions herein are comprised of at least one macular pigment selected from the group of lutein, including its isomers, and/or zeaxanthin including its isomers, such as meso-zeaxanthin and/or R,R-zeaxanthin, and/or salts and/or metabolites thereof, and the like. The macular pigments may be derived for example from a plant extract and/or oleoresin containing xanthophylls and/or xanthophylls esters. Generally, the macular pigments (carotenoids) are useful for nutrition and health applications, such as for example being formulated into a macular carotenoid composition with other active ingredient(s), nutrient(s), and/or excipient(s).

In one embodiment, a macular carotenoid composition may include macular carotenoids, where of the amount of macular carotenoids at least 80% by weight being trans-lutein, at or about 6% by weight being (R,R)-zeaxanthin and at or about 6% by weight being (R,S)-zeaxanthin (meso-zeaxanthin). The remaining may be other carotenoids. The composition may contain of the amount of macular carotenoids, at or about 85% by weight trans-lutein, at or about 4% by weight (R,R)-zeaxanthin, and at or about 5% by weight (R,S)-zeaxanthin (meso-zeaxanthin). The macular pigments may be derived from the plant extract and/or oleoresin containing xanthophylls and/or xanthophylls esters, which is safe for human consumption. Such composition may comprise of the amount of macular carotenoids, trans-lutein content of at least 85% or at or about 85%, and the ratio of trans-lutein and zeaxanthin isomers is in the range of at or about 4:1 to at or about 6:1. The ratio of the isomers of zeaxanthin (e.g. meso-zeaxanthin and R,R-zeaxanthin) is in the range of at or about 80:20 to at or about 20:80. The composition is administered to a subject in need thereof suffering from visual fatigue or showing symptoms of visual fatigue, such as dry eyes, visual discomfort, disturbed sleep pattern and/or visual stress.

In one embodiment, macular carotenoid compositions herein and methods of treatment herein using the compositions, may be administered to a subject in need thereof, in a form of a nutraceutical carrier, food supplement, beverage, medical food, while employing dosage forms such as granules, powders, sachets, beadlets, capsules, soft gel capsules, tablets, solutions, suspensions, and the like. The active carotenoid(s) of the compositions may be prepared by an extraction process and formulated into a composition, such as together with one or more other food grade excipient(s) and/or materials to obtain the desired form.

In one embodiment, methods of treatment herein may comprise administering an effective amount of macular carotenoids to subjects in need thereof, to relieve visual fatigue and/or symptoms of fatigue such as visual discomfort, dry eyes, and/or disturbed sleep, occurring as a result from exposure to blue light, sun rays, and/or lights of varying wavelengths and/or intensities.

In one embodiment, methods of treatment herein may comprise administering an effective amount of macular carotenoids to subjects in need thereof for protection and treatment from visual fatigue, and evaluating one or more parameters, such as contrast sensitivity, glare disability, visual processing ability and/or MPOD, and checking the effect(s) on improvement of visual health.

Compositions and methods herein can protect from visual fatigue, when symptoms of fatigue are evident in subjects exposed to light sources of varying wavelengths and intensities, selected from the group of, but not limited to, electronic devices emitting blue light, UV light, flickering light, traffic signals, electronic equipment, and the like, and/or combinations thereof.

Compositions and methods herein can treat visual fatigue, when subjects exposed for a prolonged period of time to light sources of varying wavelengths and intensities are suffering from visual discomfort, lowered MPOD, reduced contrast sensitivity, and/or disturbed visual processing speed.

In an embodiment, subjects in need of protection or treatment of visual fatigue are identified and administered with an effective amount of a macular carotenoid composition, such that a daily dose of lutein alone, or zeaxanthin alone, or isomers thereof, or combinations thereof is provided to improve visual health.

In some embodiments, methods for protection and treatment of visual fatigue herein and the compositions used herein, are comprised of evaluating one or more visual parameters by different techniques such as gene expression analysis, effect on antioxidant markers catalase, and/or choline esterase, including in-vitro tests to check the effect(s) on improvement in visual health. Such results are obtained from studies using cell lines, by exposing cell lines to specific dose of UV radiations, administering the compositions, and checking effect on gene expressions with respect to up-regulation or down-regulation of genes.

Methods and compositions as used herein are also evaluated for improvement in sleep quality in young healthy volunteers by checking the effect of 3 months supplementation of a macular carotenoid composition on MPOD levels, and assessing its effect on sleep patterns. Sleep quality is evaluated with the Pittsburgh Sleep Quality index (PSQI), a 19-item self-rated questionnaire (can be found at http://www.opapc.com/uploads/documents/PSQI.pdf).

MPOD can be measured with heterochromatic flicker photometry. Measurements are conducted at baseline and 3 months and paired-samples t-tests are employed to evaluate changes in both sleep quality and MPOD.

The compositions used herein are also evaluated for effect on blue light exposure by carrying out 12 week intervention trial with subjects. The evaluations are carried out at baseline (t=0) and at the final visit (t=12 weeks). Parameters including MPOD determination (heterochromatic flicker photometry technique), Hermann Grid (HG) for Contrast Sensitivity (CS), and Temporal visual performance assessment (CFF-critical flicker fusion frequency which indicates speed of visual processing) are evaluated during such study to assess efficacy in improving visual function.

The methods described herein also evaluate the effect of carotenoid composition in healthy volunteers during 12 month supplementation trial to check effects on visual health and visual acuity. The parameters assessed are speed of processing, contrast sensitivity, visual discomfort, disability glare assessment, and photostress recovery. Thus, the effect of compositions on the protection and treatment of visual fatigue is assessed by different in-vitro and in-vivo techniques.

While the compositions and methods herein have been described in terms of specific illustrative embodiments, any modifications and equivalents that would be apparent to those skilled in the art are intended to be included within the scope of the methods and compositions herein. The details of the methods and compositions herein, its objects, and advantages are explained hereunder in greater detail in relation to non-limiting exemplary illustrations.

EXAMPLES

Exposure to solar ultraviolet radiation is believed to increase oxidative stress and may cause oxidative damage to retinal pigment epithelial (RPE) cells. UV light triggers a number of deleterious cellular responses in retinal cells that lead to changes in gene and protein expression. Macular carotenoids play a functional role in the macula and retina of the eye. Optimal levels of macular carotenoids may reduce the risk of macular degeneration, due in large part to their antioxidant properties and ability to absorb light within the UV range.

Experiment 1

In Vitro Study to Show Effect of Carotenoids on UV Exposure and Effect on Gene Expression Analysis Retinal pigment epithelial (RPE) cells play a key protective role by shielding retina from damaging UV rays and are used as a model to study the effect of macular carotenoids. In this study, a human RPE cell line (ARPE-19 cells were acquired from American Type Culture Collection (ATCC)) was either treated with placebo or treated with macular carotenoids alone or in combination for 24 hours prior to UV exposure. Cells were maintained for another 18 hours, then harvested for gene expressions. In another study, acetylcholinesterase and catalase activities in the presence of macular carotenoids were tested. The purpose of the studies is to exhibit the effect of UV irradiation on gene expression of cells, which are exposed or not exposed to lutein.

According to Study 1, Cell line ARPE-19 was subjected to 24 hour pretreatment with 10 μM lutein, followed by exposure to UV radiation of 1 $J/m^2$ for 7 seconds.

According to Study 2, Cell line ARPE-19 was subjected to 24 hour pretreatment with 10 μM lutein, followed by exposure to UV radiation of 300 $J/m^2$ for 10 minutes.

Gene expression analysis was carried out in response to UV exposure and macular carotenoid administration. It was observed that some of the genes were up-regulated (enhanced), while some of the genes were expressed as down-regulated (inhibited), in response to same dose of carotenoid, but different dose of UV exposure.

Up-regulated genes expression demonstrated that:
UV exposure without lutein enhances gene expression exhibiting inflammation, oncogenesis and DNA damage.
Lutein without UV exposure inhibits oncogenesis and inflammation.
Lutein with UV exposure inhibits oncogenesis and growth factor tumor suppressors.

Down-regulated genes expression demonstrated that:
UV exposure without lutein exhibits inflammation and anti-proliferation.
Lutein without UV exposure inhibits DNA damage and inflammation.
Lutein with UV exposure inhibits inflammation.

Result: In an in-vitro model, macular carotenoids treatment inhibited cholinesterase activity and enhanced catalase activity. It was observed that mild UV irradiation affected significant changes in gene expressions, including down regulation and up-regulation of certain genes that support neurophysiologic processes in vision. Gene expression analysis indicates lutein plays a protective role for vision health. Thus it was observed that macular carotenoid treated cells may ameliorate the effects of mild UV irradiation on RPE cells, as shown by expression of genes involved in cell proliferation, inflammation, immune function, and wound healing in this study.

In the following experiments, the macular carotenoid composition evaluated had relative amounts of lutein and zeaxanthin isomers in the ratio of 5:1. The zeaxanthin isomers include R,R-zeaxanthin and meso-zeaxanthin, for example in relative amount of the zeaxanthin isomers at about 75% to 25% respectively. The macular carotenoid compositions including this ratio were formulated in the form of a molecular dispersion comprising hydrophilic carrier, stabilizer and surfactant. The molecular dispersion is in the form of free flowing powder, which is then suspended in suitable oil medium such as sunflower oil, safflower oil to form oil suspension, which is then filled in soft gel capsules as final dosage form. This formulation is evaluated in the following in-vivo examples. In some examples herein, references made herein to compositions of Lutemax2020 are a composition of the Applicant, which is disclosed for example in co-pending U.S. patent application publication 2011/0065805, and which is incorporated by reference herein.

Experiment 2

Effect of Macular Carotenoids on Sleep Quality

The non-image forming photopigmentmelanopsin is found in intrinsically photosensitive retinal ganglion cells (ipRGCs), where it has been shown to play a role in circadian rhythm entrainment, presumably by detecting the presence of sunlight. The small amounts of light from electronic devices pass through the retina into a part of the hypothalamus (the area of the brain that controls several sleep activities) and delay the release of the sleep-inducing hormone, melatonin. This affects sleep pattern and shifts the body's natural clock, known as the circadian rhythm. A healthy MPOD blocks harmful blue light from reaching the visual cells of the macula. MPOD is associated with visual performance benefits like glare, bright light, and night driving.

As macular pigments (MP) and melanopsin both preferentially absorb short-wave light, experiments herein address the question of whether increasing participants' MP optical density (MPOD), via macular carotenoid supplementation for 3 months, would affect sleep quality.

Methods: This was a 3-month, double-blind, placebo-controlled trial in which 45 young (aged 18-25 yrs.), healthy individuals participated. Random assignment was used to determine the carotenoid supplement group (n=30) and the placebo group (n=15). Those in the carotenoid supplement group ingested daily a capsule containing 22 mg lutein and 5 mg zeaxanthin isomers, whereas participants in the placebo group took an inert capsule. The capsule is a formulation of the macular carotenoids as a solid molecular dispersion, where it contains excipient(s) used to prepared solid dispersion of lutein and zeaxanthin, the dispersion is suspended in oil as described above. Sleep quality was evaluated with the Pittsburgh Sleep Quality index (PSQI), a 19-item self-rated questionnaire. MPOD was measured with heterochromatic flicker photometry. Measures were conducted at baseline and at 3 months; paired-samples t-tests were employed to evaluate changes in both sleep quality and MPOD.

Results: At baseline, sleep quality and MPOD were not found to be significantly related (r=0.112; p=0.46). For the 3-month intervention, the experimental group exhibited significant improvement in overall sleep quality (t=2.95; p=0.0063) and MPOD (t=−5.19; p<0.001). The placebo group did not change for either of these variables over the study period (p>0.50 for both). It is appreciated that "r", "p" and "t" represent universal statistical notations, which are used while treating data and to define significance of the result, in particular, where "p" represents the probability, "r" is Pearson's correlation, and "t" is t-test value. Reference is to http://users.sussex.ac.uk/~grahamh/RM1web/APA%20format%20for%20statistical%20notation%20and%20other%20things.pdf.

Conclusions: It is perhaps the case that increases in MPOD serve to absorb more short-wave (blue) light from sources (such as computer screens, tablets, or smartphones) that can be used during night-time hours, and would otherwise provide a circadian signal to stay awake. Although the lack of a significant correlation between MPOD and sleep quality at baseline is not consistent with this conclusion, it may be that acute, relatively rapid increases in MPOD are not immediately compensated for by the ipRGC circadian rhythm system, and therefore manifest as improvements in sleep quality.

Experiment 3

In-Vivo Evaluation of Macular Carotenoids Composition for Effect on Blue Light Exposure Study Design: 12 week intervention trial was carried out with 49 healthy, non-smoking subjects (18-25 yrs), out of which 14 were administered with placebo and 35 volunteers were administered carotenoid composition (lutein (L) 20 mg, zeaxanthin isomers (Zi) 4 mg. The zeaxanthin isomers include R,R zeaxanthin and meso-zeaxanthin, where the relative percentage of the 4 mg is 75:25. The composition is in the form of a soft gel capsule, in which the composition is present in the form of oil suspension. The evaluations were carried out at baseline (time=0) and at final visit (time=12 weeks). Evaluations were MPOD determination (heterochromatic flicker photometry technique), Hermann Grid (HG) Contrast Sensitivity (CS), and temporal visual performance assessment (CFF-critical flicker fusion frequency which indicates speed of visual processing).

Subjects meeting the following criteria were considered for the study: The subjects having high blue-light exposure, e.g. screen time, including for example playing engaging, cognitively-tasking, e.g. video games (e.g., "first-person shooters") at least 4 hours/day were selected for this study. Such subjects should also have at least 2-3 hours of outside activity/day. MPOD of subjects should be about 0.69 and the subjects should be complaining of at least one or more of the following problems: Accommodative issues (difficulty seeing in the distance after prolonged near-work), digital eye-strain and other vision issues, such as blurred vision, difficulty in focusing, dry and irritated eyes, headaches, neck pain, and/or back pain.

The subjects were administered the composition or the placebo and the groups were compared for the following end points with respect to treatments, where the end points are evaluation parameters, used to observe the effect of the compositions herein on improvement of visual function:

TABLE 1

End point evaluation in subjects administered with composition or placebo
(N = 49, Mean ± Standard Deviation)

| End Points | Placebo N = 14 | L/Zi N = 35 | Significance |
|---|---|---|---|
| MPOD | −0.0033 ± 0.013 | 0.029 ± 0.03 | P < 0.001 |
| CFF | 0.267 ± 0.8 | 1.043 ± 0.99 | P < 0.0012 |
| CS | 0.090 ± 5.5 | 10.11 ± 8.6 | P < 0.0002 |
| Sleep | 0.143 ± 1.7 | −0.86 ± 1.33 | P < 0.0335 |
| Screen/Electronic devices/Outdoor exposure | 0.64 ± 3.7 | −1.57 ± 6.4 | P < 0.0231 |

FIG. 1 shows the effect of the composition on MPOD. It was observed that the subjects administered with the composition exhibited significantly increased MPOD as compared to those who were administered placebo as per the study design. MPOD values are on the y-axis.

Figure 2:
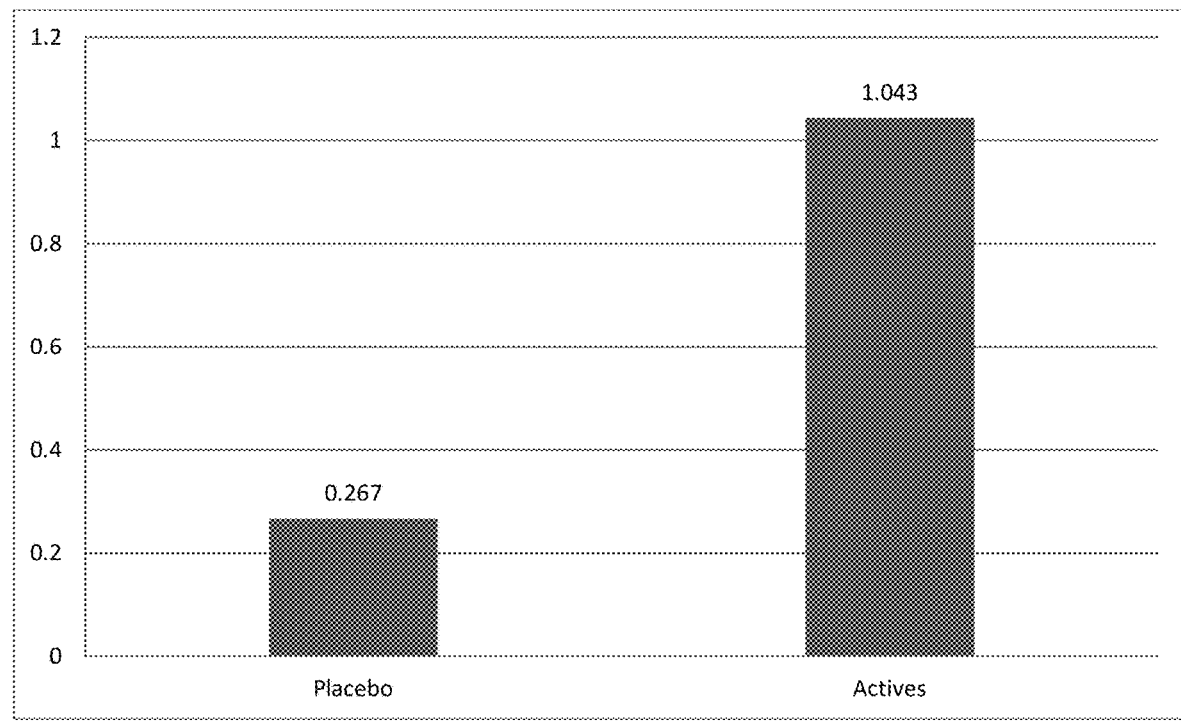
FIG. 2 shows the effect of a composition herein on (CFF).

FIG. 2 shows the effect of the composition on CFF. It was seen that the subjects administered with the composition had enhanced CFF as compared with placebo administration. CFF units on the y-axis are in Hertz (Hz).

Figure 3:
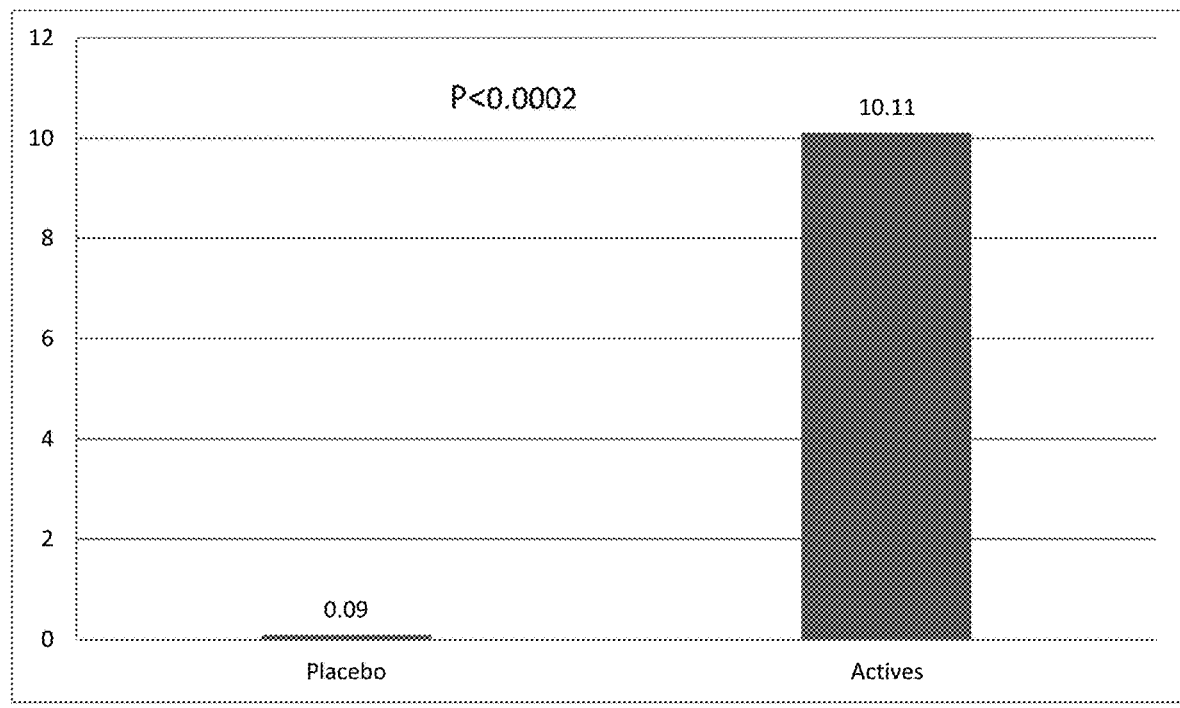
FIG. 3 shows the effect of a composition herein on contrast sensitivity (CS).

FIG. 3 shows the effect of the composition on contrast sensitivity. The subjects exhibited enhanced CS, when administered with the composition. CS values are represented on the y-axis as percent contrast.

Figure 4:
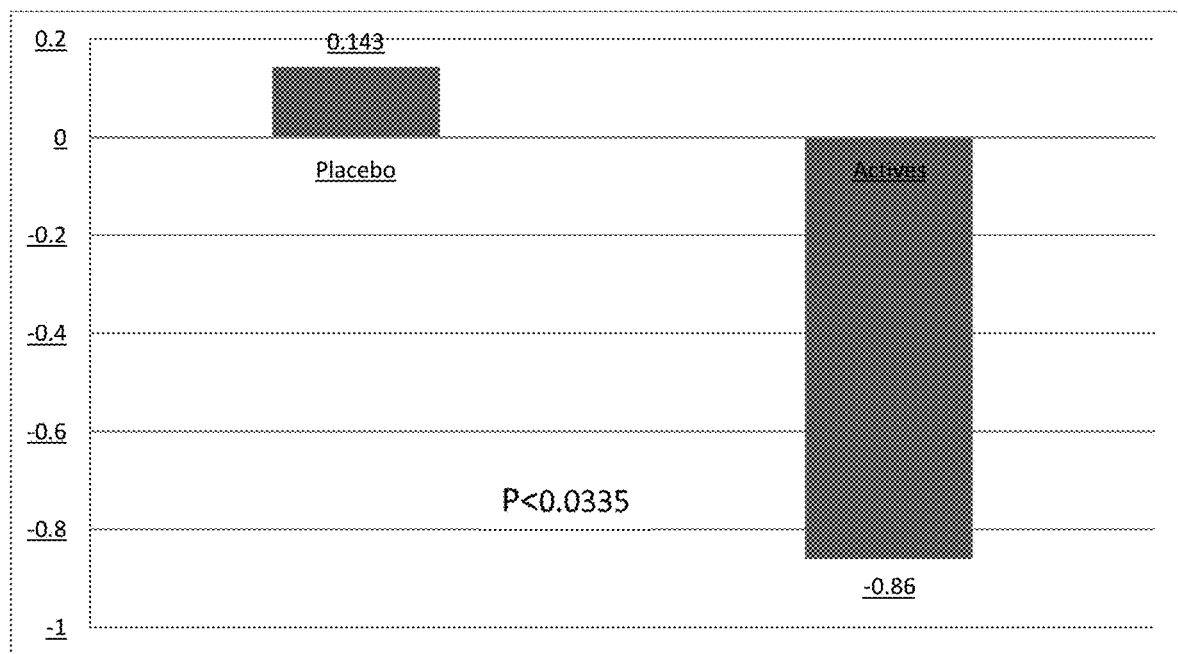
FIG. 4 shows compositions herein improve sleep.

FIG. 4 shows the composition also improves sleep, as per the MPOD values on the y-axis.

Figure 5:
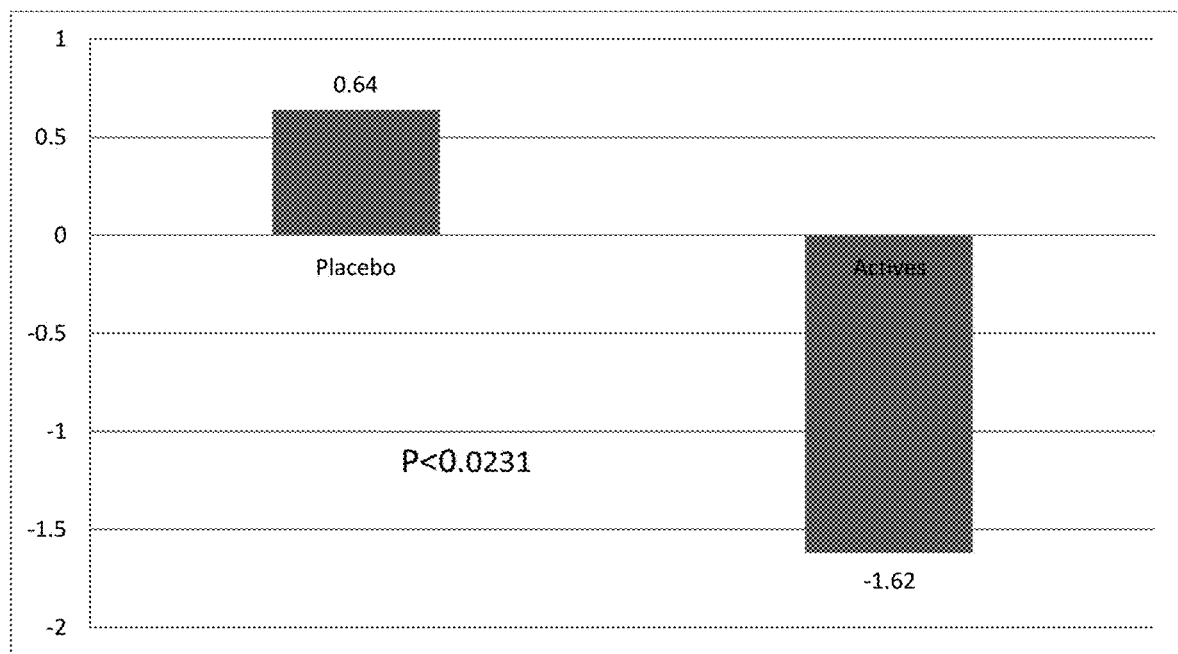
FIG. 5 shows compositions herein decreased screen/electronic devices/outdoor exposure.

FIG. 5 shows the compositions also decreased Screen/Electronic devices relative to Outdoor exposure. The y-axis represents relative time (e.g. hours). This means that, as the composition improves the sleep pattern, subjects will try to go to sleep early, thus decreasing the work time and exposure to screen and electronic devices, also due to reduced fatigue the subjects will be energized and spend time more in outdoor activities.

TABLE 2

Change from Baseline (t test)

| End Points | Placebo N = 14 | | L/Zi N = 35 | |
|---|---|---|---|---|
| | Mean | P value | Mean | Significance |
| MPOD | −0.003 ± 0.013 | 0.3782 | 0.029 ± 0.03 | p < 0.0001 |
| CFF | 0.267 ± 0.77 | 0.2215 | 1.043 ± 0.99 | p < 0.0001 |
| HG | 0.090 ± 5.49 | 0.9521 | 10.10 ± 8.5 | p < 0.0001 |
| Sleep | 0.14 ± 1.70 | 0.7586 | −0.86 ± 1.33 | p < 0.0006 |
| Screen/Electronic devices/Outdoor exposure | 0.64 ± 3.66 | 0.5232 | −1.57 ± 6.38 | 0.1547 |

Figure 6:
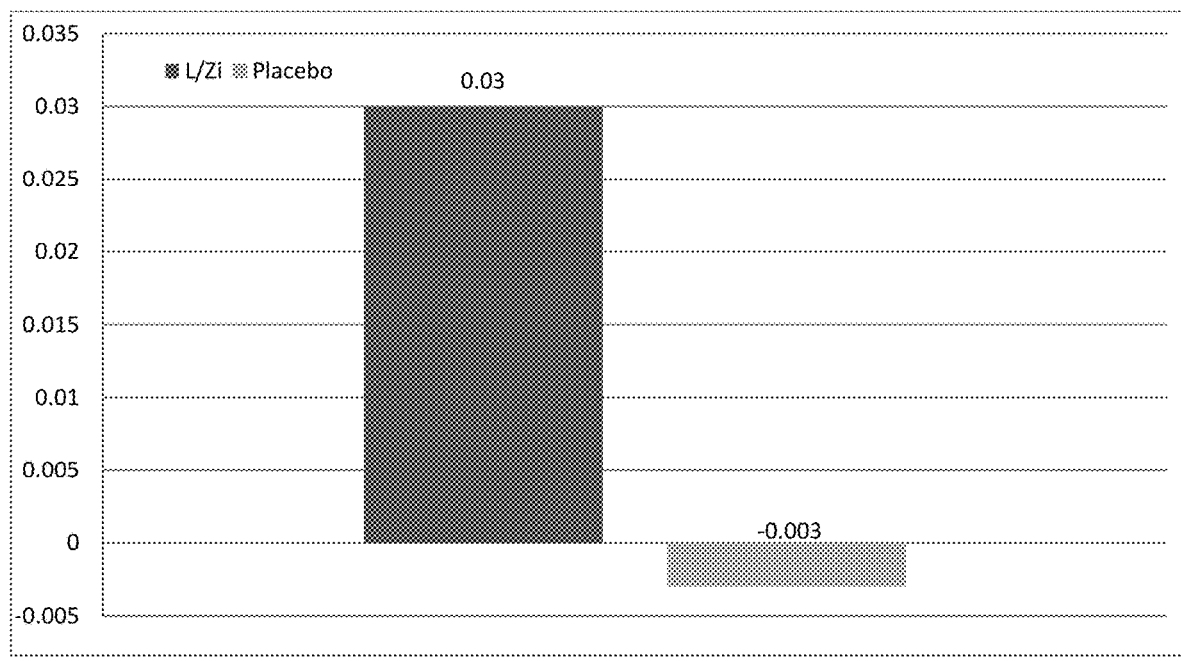
FIG. 6 shows compositions herein increased MPOD in Subjects Who are Exposed to Blue Light for more than 4 h (Outdoor and Indoor).

FIG. 6 shows the compositions increased MPOD in subjects who are exposed to blue light for more than 4 hours (Outdoor and Indoor). MPOD values are on the y-axis.

Figure 7:
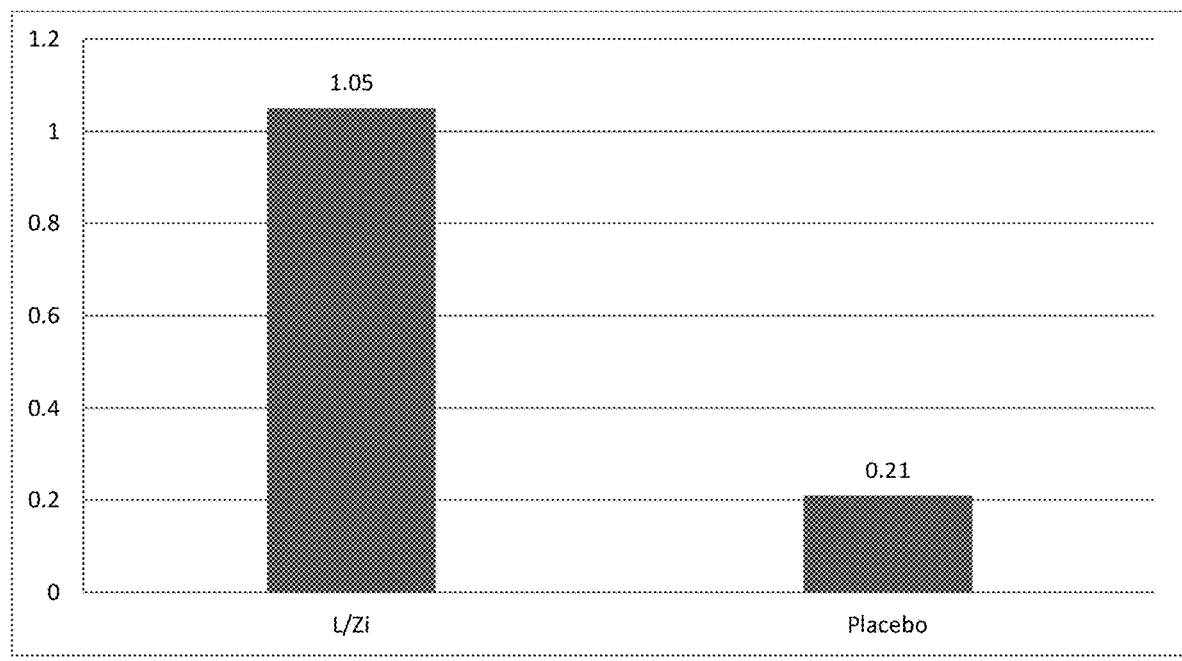
FIG. 7 shows compositions herein enhance critical flicker fusion (CFF) in subjects exposed to blue light≥4 h (Outdoor and Indoor)

FIG. 7 shows the composition enhances CFF in subjects who are exposed to blue light≥4 hours (Outdoor and Indoor). CFF values are on the y-axis represented by Hertz (Hz).

Figure 8:
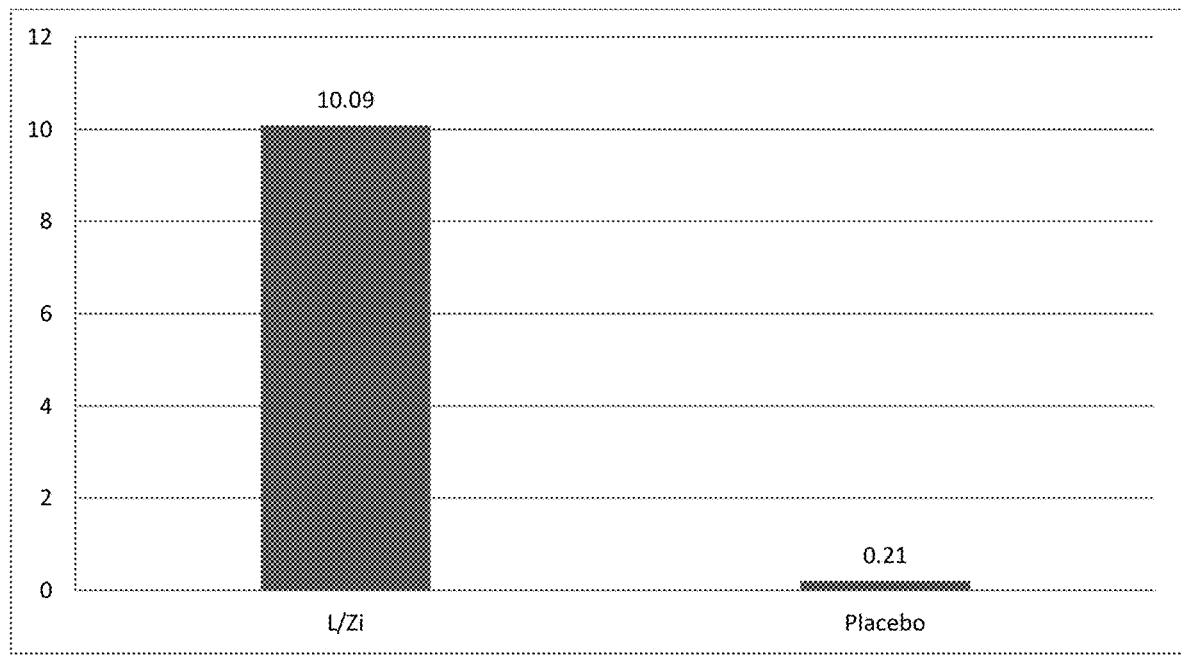
FIG. 8 shows carotenoid compositions herein increase CS in subjects exposed to blue light for≥4 h (Outdoor and Indoor).

FIG. 8 shows the carotenoid compositions increase CS in Subjects who are exposed to Blue Light for≥4 hours (Outdoor and Indoor). CS values are represented on the y-axis as percent contrast.

Figure 9:
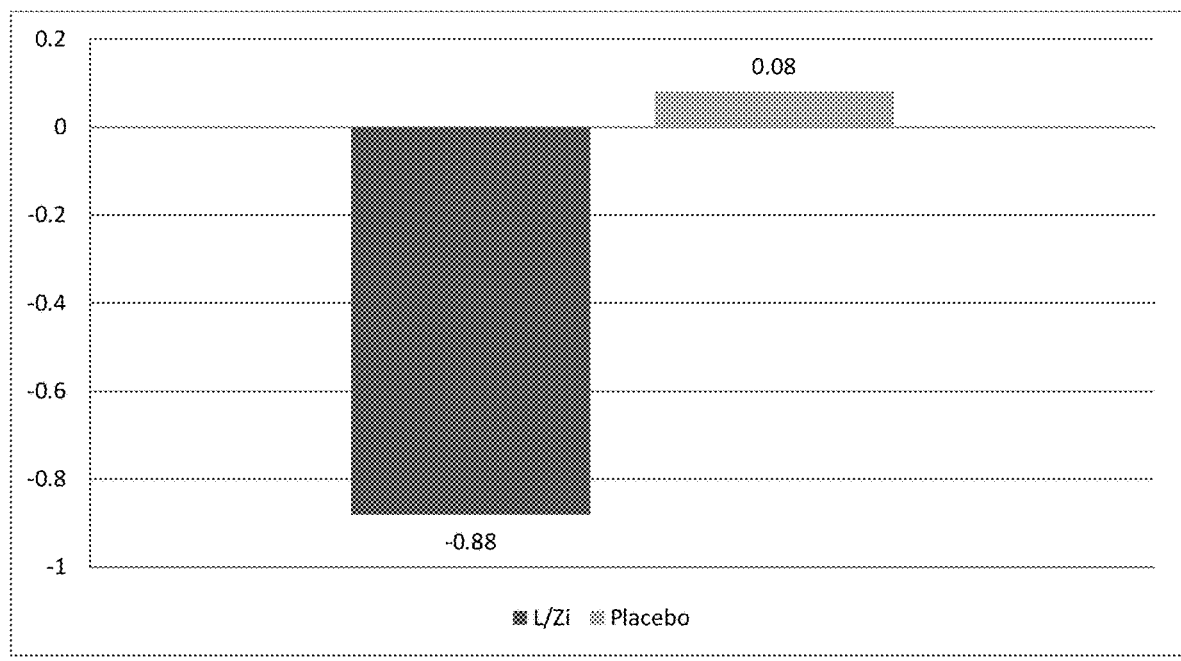
FIG. 9 shows that carotenoid compositions herein improved sleep in subjects exposed to blue light≥4 h (Outdoor and Indoor).

FIG. 9 shows the carotenoid compositions improved sleep in subjects who are exposed to blue light≥4 hours (Outdoor and Indoor). MPOD values are on the y-axis.

Experiment 4

In-vivo Evaluation of Carotenoid Composition for Effect on Visual Performance/Fatigue This study was designed as a double-blind, placebo controlled, 12-month carotenoid supplementation trial, in which effects on visual performance and visual acuity was assessed. Sixty (60) subjects were followed throughout the study period. Two levels of daily lutein supplement: 10 mg & 20 mg was used, with subject numbers as follows: 20 mg lutein group (n=25), 10 mg lutein group (n=25), and placebo (n=10). In the compositions, along with lutein, zeaxanthin isomers were combined, where at 20 mg lutein, there was 4 mg of zeaxanthin isomers, at 10 mg lutein there was 2.5 mg of zeaxanthin isomers. The composition was in the form of soft gel capsules containing solid dispersion of macular carotenoids suspended in suitable oil medium.

At visit 1, subjects were administered with informed consent and a screening questionnaire. The participant's visual acuity was tested to confirm eligibility.

The following are specific aims for the study. Detailed procedures are described below.

1. Characterize macular pigment (MP) levels in a total of 60 university student subjects, aged 18-25. MP measured via heterochromatic flicker photometry. Assess MP levels over a period of 12 months' lutein supplementation, in 3 groups: 1) 20 mg lutein daily (n=25), 2) 10 mg lutein daily (n=25), 3) placebo (n=10).

2. Assess visual performance parameters thought to be affected by ocular/brain lutein:
   a. Speed of processing
   b. Contrast sensitivity
   c. Visual discomfort
   d. Disability glare assessment
   e. Photostress recovery 3. Assess serum levels of lutein, via high performance liquid chromatography (HPLC), across the study period.

Initial Screening

Visual Acuity: During the first visit only, participants were asked to stand behind a tape mark, which is positioned at a distance of approximately 20 feet from a standard wall chart. Under standard room lighting conditions, participants were asked to read the lowest line they can resolve on the chart with both eyes open. Following that measurement, participants were asked to cover the left eye and read the lowest resolvable line using only the right eye. Following that measurement, participants were asked to cover the right eye and read the lowest resolvable line using only the left eye. Subsequent vision testing was usually conducted in only one eye (usually the right eye), as one of the primary outcome measures (macular pigment optical density-MPOD) is approximately the same in both eyes. If the right eye has visual acuity poorer than 20:60, but binocular visual acuity is 20/30 or better, the left eye was used for measuring MPOD instead of the right eye.

Inclusion/exclusion criteria questionnaire: Participants were asked to complete a short questionnaire to determine eligibility for the study. Questions are related to the "exclusionary criteria" noted above (subject's smoking status, body-mass index, pregnancy status, nutritional supplementation status (especially lutein and/or zeaxanthin), eye disease status, and potential digestive issues. The following are specific issues to be addressed:

Exclusionary criteria: Subjects meeting the following criteria will not be enrolled in the study.

1. Body Mass Index of 27 or greater. In an overweight individual, the supplemental lutein may be deposited preferentially in adipose tissue, and not in the retina.
2. Macular pigment optical density (MPOD) of 0.70 or higher. Individuals with very high MPOD may be approaching saturation levels, and therefore not exhibit changes reflective of lutein supplementation. They would therefore be excluded from the study. The 0.70 criterion is a level from which subjects can typically increase appreciably upon supplementation.
3. Ocular disease or insufficient visual acuity. Subjects will undergo an initial visual screening, and if either of these situations is evident, the subject was excluded from the study. Visual acuity of 20/30 best corrected is cutoff for exclusion.
4. Systemic disease. If a subject is currently in a disease state (e.g. diabetes), then s(he) was precluded from participating in the study.
5. Smoking status. Current smokers were excluded from the study. Smoking has been shown to have deleterious systemic health effects, and (germane to our proposal) is inversely related to MPOD level. The ability of smokers to accumulate supplemented lutein in the retina could be compromised.

Subject testing (5 visits over 1 year): baseline, 3 months, 6 months, 9 months, and 12 months;

1. Macular Pigment Optical Density (MPOD)/critical flicker fusion threshold testing (conducted at each of 5 visits). In order to measure MPOD, participants were seated comfortably in front of a desktop measurement device. Participants were asked to place their chin in a chin rest, which optimizes alignment for viewing the stimulus. The stimulus itself is composed of two wavelengths of light: 460 nm (shortwave "blue" light, strongly absorbed by macular pigment-MP) and 550 nm (midwave "green" light, not absorbed by MP), which appear to participants as either a small blue-green disk or a small, blue-green ring, depending on where in the fovea MPOD is being measured. The two wavelengths were presented in counter-phase, which gives the disk the appearance of flicker. In order to minimize the flicker, participants are asked to use a knob to adjust the intensity of the 460 nm component of the disk. Participants with a denser MP layer will require more intense 460 nm light to match the luminance of the 550 nm light, as MP was filtering a significant portion of the 460 nm light. MPOD was then calculated as the logarithm of the intensity of shortwave light needed to match the luminance of mid-wave light in the center of the retina, where MP is densest, when compared to the logarithm of the intensity needed in the parafovea, where MP was virtually absent.
2. Dietary Questionnaire (conducted at each of 5 visits). A brief questionnaire concerning participants' dietary intake of foods that contain lutein was administered during each visit.
3. Visual Performance Measures (conducted at baseline, 6 months, and 12 month visits). Note: All light stimuli were well below the ANSI Z-136 safety standard for exposure to intense light. At the highest possible level, the LED lights proposed for use in this study are $\frac{1}{20}^{th}$ the intensity level of the safety standard.
   a. Disability glare performance
      This visual performance task involves determining a subject's ability to see "through" glare produced by lights presented in the periphery. The experimental apparatus was a ring of white LED lights through which the subject will look and attempt to identify the orientation of a black and white grating stimulus (either tilted left, right, vertical, or horizontal). The intensity of the LEDs was gradually increased (via computer control) until the subject indicates the s(he) can no longer determine the orientation of the grating. The grating was presented on a computer screen, and flashed every 500 milliseconds, with the orientation randomized.
   b. Photostress recovery performance
      This task was to assess the visual recovery time elapsed after a subject is exposed to a relatively bright light for 3 seconds. The experimental apparatus was a solid disk of white LEDs that, when illuminated, appear circular and subtend approximately 5 degrees of visual angle. The subject was instructed to look at the disc of light for 3 seconds, and then indicate when s(he) can detect the orientation of a grating stimulus (described above).
   c. Visual discomfort assessment
      This task was convolved with the "Photostress recovery performance" task. After exposure to the bright disc of light (and while waiting to visually reacquire the target) the subject was asked to rate their level of discomfort experienced during the light exposure. Prior to testing, subjects was familiarized with a rating scale, ranging from 0 (no discomfort) to 10 (very difficult to tolerate).
   d. Contrast sensitivity testing
      This task involves subjects' adjustment of a black-on-white checkerboard stimulus until they can just detect the presence of illusory patches at the junctions of squares. This is a well-known illusion called the Hermann Grid illusion, and is thought to reflect inhibitory visual processes.

Composition Administration and Supplementation Regimen. Once vision testing and the blood draw have been completed, an investigator provided carotenoid composition to the participant containing either a nutritional supplement made of 10 mg, or 20 mg of lutein (and zeaxanthin isomers) or a placebo (containing no active).

Data Analysis

Data was analyzed via traditional statistical methods (e.g. correlation, analysis of variance (ANOVA)). Blood parameters were analyzed.

Statistical Considerations and Analyses. A power analysis was conducted using an ideal 1-β of 0.80 and α=0.05 (for a directional t-test). An expected mean change in serum concentrations in lutein of about 60%, and in MP density of about 35% would suggest a need for approximately 25 participants in the two treatment groups to detect significant effects, should they exist. As demonstrated in numerous studies (e.g. Landrum et al. 1997), when subjects consume a placebo, neither their serum nor retinal levels of lutein change appreciably. Because these measures are two of the outcome measures, and because interest was in the change in serum/retinal concentrations of lutein, a smaller (n=10) placebo (control) group was employed. Analysis was conducted by an independent, masked statistician. Comparisons were made between groups (supplement vs. placebo) using time-series analysis and ANOVA. Correlational analyses were conducted among all variables, in order to test for potential significant relationships.

Results

Vision Health: Macular carotenoid composition improved contrast sensitivity (CS), both doses significantly changed CS relative to the baseline. At 12 months both doses have significant effect on CS over the placebo.

Figure 10:
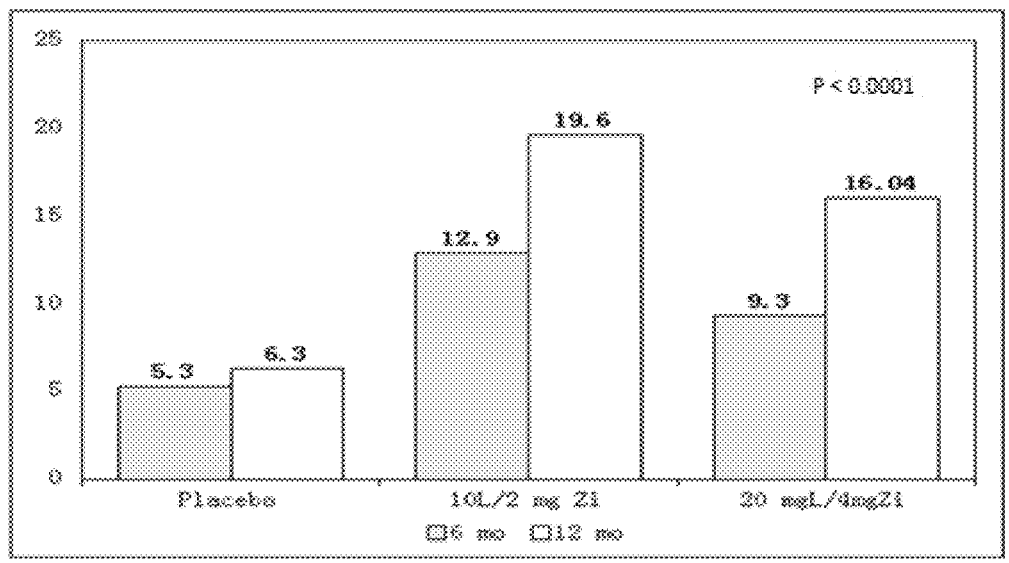
FIG. 10 shows increase of contrast sensitivity using a composition herein.

FIG. 10 shows the effect of the composition on CS over placebo. The composition significantly changed CS from baseline. The y-axis represents the percent contrast.

Figure 11:
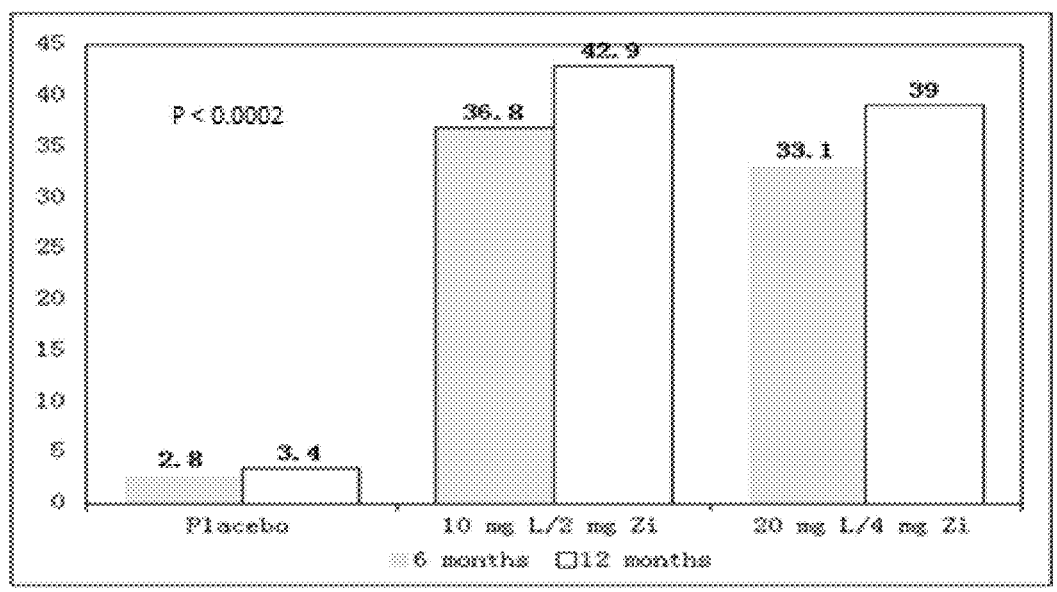
FIG. 11 shows improvement of glare performance from a composition herein.

FIG. 11 shows the effect of the composition on visual glare. The composition improved glare performance at both doses relative to the baseline (see y-axis value increases in bar graph). At 6 and 12 months both doses have significantly improved glare performance over the placebo.

Figure 12:
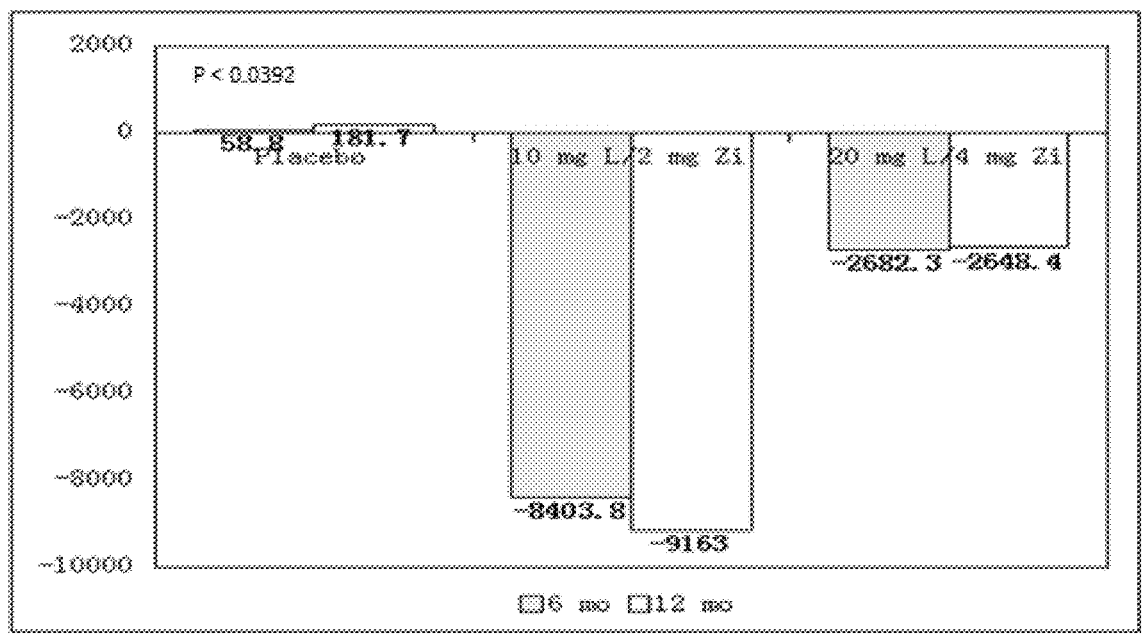
FIG. 12 shows improvement of photo stress recovery from a composition herein.

FIG. 12 show the effect of the composition on photo-stress recovery. The y-axis represents milliseconds. The composition exhibited better photo stress recovery at both the doses relative to the baseline. At 6 and 12 months, 20 mgL/4 mg Zi have significantly improved better photo stress over the placebo.

Figure 13:
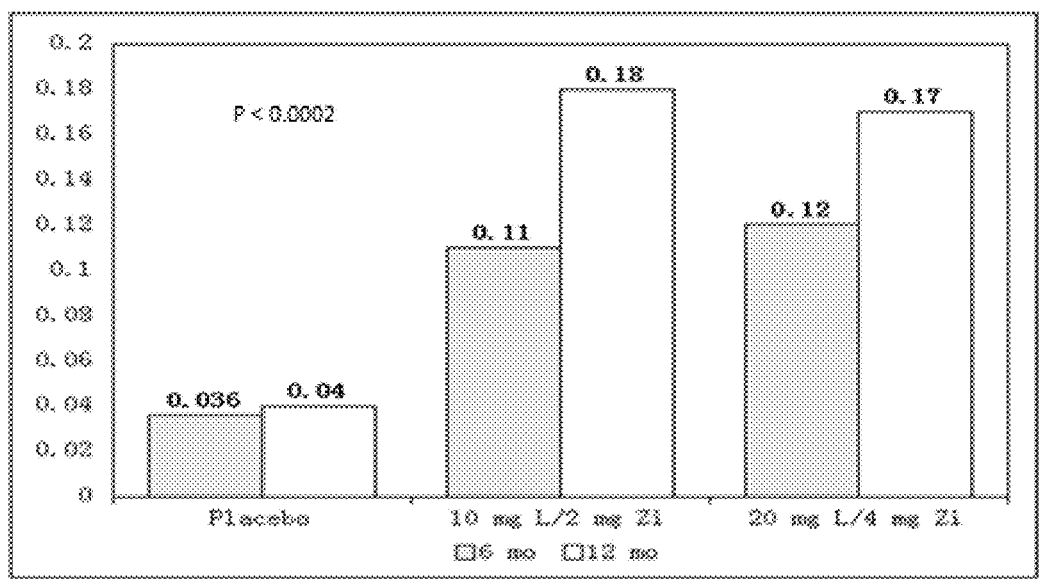
FIG. 13 shows the increase of MPOD over a baseline using a composition herein.

FIG. 13 shows the effect of the composition on MPOD. Lutemax2020 improved MPOD at both doses. At 6 and 12 months, 10 mgL/2 mg Zi and 20 mgL/4 mgZi have significantly improved MPOD over the placebo. MPOD values are on the y-axis.

With regard to the foregoing description, it is to be understood that changes may be made in detail, without departing from the scope of the present invention. It is intended that the specification and depicted embodiments are to be considered exemplary only, with a true scope and spirit of the invention being indicated by the broad meaning of the claims.

The invention claimed is:

1. A method for improvement in visual function in a subject, comprising:
   (a) identifying a subject in need thereof, exposed to light of varying wavelengths and intensity and suffering from visual fatigue in the form of visual discomfort, visual stress, and affected sleep quality,
   (b) administering to the subject a daily dose of macular carotenoids in an amount effective to enhance critical flicker fusion frequency, contrast sensitivity, and macular pigment optical density in the subject as compared to those of a subject that has been exposed to light of varying wavelengths and intensity and suffering from visual fatigue in the form of visual discomfort, visual stress, and affected sleep quality but has not been administered with the macular carotenoids, the macular carotenoids consisting of at least 1mg of lutein and of at least 0.2 mg of zeaxanthin isomers, the zeaxanthin isomers including meso-zeaxanthin and R,R zeaxanthin, and the ratio of lutein and zeaxanthin isomers is 5:1, and the ratio of (R,R)-zeaxanthin and meso-zeaxanthin is in the range of at or about 80:20 to at or about 20:80, wherein the zeaxanthin isomers and lutein are the only active agents administered to the subject, and wherein the zeaxanthin isomers and lutein are derived only from marigold; and
   (c) measuring at least one parameter of the subject selected from the group consisting of contrast sensitivity, disability glare, visual processing speed, and photostress recovery; and
   (d) evaluating an improvement in visual function of the subject.

2. The method as in claim 1, wherein the subject in need thereof is exposed for an extended time period to light of varying wavelength and intensity, including one or more of blue light from electronic devices, sun rays, and any light emitting source selected from the group of lights, street lights, decorative lights, and combinations thereof.

3. The method according to claim 1, wherein the subject in need thereof has decreased macular pigment optical density and suffering from affected sleep quality.

4. The method according to claim 1, wherein the subject in need thereof is suffering with visual discomfort due to lowered contrast sensitivity.

5. The method according to claim 1, wherein the subject in need thereof is affected with visual stress due to lowered visual processing speed.

6. The method according to claim 1, wherein the subject in need thereof is suffering from visual fatigue due to lowered disability glare and photostress recovery.

7. The method according to claim 1, wherein the subject in need thereof is administered with a daily dose of the macular carotenoids, the macular carotenoids consisting of 1 mg lutein and 0.2 mg of zeaxanthin isomers, the zeaxanthin isomers including meso-zeaxanthin and R,R zeaxanthin.

8. The method according to claim 1, wherein the subject in need thereof is a mammal.

9. The method according to claim 1, wherein the subject in need thereof is a human.

* * * * *